US011793622B2

(12) United States Patent
Dalton et al.

(10) Patent No.: US 11,793,622 B2
(45) Date of Patent: Oct. 24, 2023

(54) ARTIFICIAL INTERSTITIUM DEVICE

(71) Applicants: Michael J. Dalton, Evanston, IL (US); Jordan M. Dalton, Libertyville, IL (US); Natan A. Pheil, Highland Park, IL (US); Melanie Graham, Edina, MN (US)

(72) Inventors: Michael J. Dalton, Evanston, IL (US); Jordan M. Dalton, Libertyville, IL (US); Natan A. Pheil, Highland Park, IL (US); Melanie Graham, Edina, MN (US)

( * ) Notice: Subject to any disclaimer, the term of this patent is extended or adjusted under 35 U.S.C. 154(b) by 1080 days.

(21) Appl. No.: 16/392,328

(22) Filed: Apr. 23, 2019

(65) Prior Publication Data

US 2019/0343615 A1 Nov. 14, 2019

Related U.S. Application Data

(60) Provisional application No. 62/668,737, filed on May 8, 2018.

(51) Int. Cl.
*A61F 2/02* (2006.01)
*A61L 27/36* (2006.01)
(Continued)

(52) U.S. Cl.
CPC .......... *A61F 2/022* (2013.01); *A61L 27/3604* (2013.01); *A61L 27/54* (2013.01);
(Continued)

(58) Field of Classification Search
CPC ................ A61F 2/022; A61F 2230/008; A61F 2250/003; A61F 2250/0068;
(Continued)

(56) References Cited

U.S. PATENT DOCUMENTS

| 5,425,764 A | 6/1995 | Fournier |
| 2014/0236078 A1 | 8/2014 | Dalton |

(Continued)

FOREIGN PATENT DOCUMENTS

| WO | 2012/010767 A1 | 1/2012 |
| WO | 2017/053751 A1 | 3/2017 |

OTHER PUBLICATIONS

European Search Report for European Application No. EP 19 173 392.2 dated Oct. 8, 2019, 7 pages.

*Primary Examiner* — Paul B Prebilic
(74) *Attorney, Agent, or Firm* — Klintworth & Rozenblat IP LLP

(57) ABSTRACT

An interstitial fluid accumulation chamber is configured to be implanted in a mammal for use as a protective environment for transplanted cells. The interstitial fluid accumulation chamber includes opposed first and second members, a cell isolation chamber, and a plurality of spaced-apart members. The opposed first and second members are disposed in spaced-apart relation. The cell isolation chamber is disposed within and in-between the opposed first and second members. The cell isolation chamber includes a filter which contains pores sized to allow interstitial fluid to enter the cell isolation chamber while preventing cells within the cell isolation chamber from leaving the cell isolation chamber. The plurality of spaced-apart members are disposed within and between the opposed first and second members. The plurality of spaced-apart members form a tortuous path which is configured to prevent tissue from growing within the interstitial fluid accumulation chamber.

23 Claims, 4 Drawing Sheets

(51) Int. Cl.
*A61L 27/54* (2006.01)
*A61M 25/00* (2006.01)

(52) U.S. Cl.
CPC ........ *A61F 2230/008* (2013.01); *A61M 25/00* (2013.01); *A61M 2202/04* (2013.01); *A61M 2205/04* (2013.01)

(58) Field of Classification Search
CPC .. A61L 27/3604; A61L 27/54; A61L 2300/40; A61L 2300/62; A61L 2300/64; A61M 25/00; A61M 2202/04; A61M 2205/04
See application file for complete search history.

(56) References Cited

U.S. PATENT DOCUMENTS

| | | |
|---|---|---|
| 2015/0190620 A1 | 7/2015 | Dalton |
| 2017/0007808 A1 | 1/2017 | Dalton |
| 2017/0086963 A1* | 3/2017 | Tai .................... A61F 2/022 |
| 2018/0125632 A1* | 5/2018 | Cully .................. A61F 2/022 |

* cited by examiner

ARTIFICIAL INTERSTITIUM DEVICE

RELATED APPLICATIONS

The present application claims the priority benefit of co-pending U.S. Provisional Patent Application No. 62/668,737, filed May 18, 2018, which is incorporated by reference herein in its entirety.

FIELD OF THE DISCLOSURE

The present disclosure relates to a method and apparatus for an implanted device that promotes the protection and maintenance of transplanted cells in a host body such as a mammal. The system provides the transplanted cells with a safe, nutritious environment for survival and is also suitable for removal of waste products generated by the cells.

BACKGROUND

The prevalence of diabetes mellitus is estimated to be about 9% globally, with over 29 million diabetic patients in the US alone. Regular insulin injections are the primary therapy used to control blood glucose in patients with insufficient insulin production. Despite the improvements in exogenous insulin therapy, suboptimal glucose control is a major risk factor in development of complications, with substantial morbidity. Retinopathy affects a staggering 50% of all diabetics, and over 90% after 25 years. Kidney complication risk increases over time, with virtually all diabetic patients experiencing some degree of kidney disease at long durations, and end stage renal disease prevalence has not declined.

Age and disease dependent heterogeneous peripheral neuropathies, with or without neuropathic pain, affect approximately 25% of adult Type 1 Diabetes patients and that number climbs to 90% when diabetic autonomic neuropathy is included. As a result, patients experience a lower quality-of-life together with substantial burden in managing chronic disease. Even considering the most sophisticated injected insulin strategies, it is becoming increasingly evident that C-peptide is a critical factor in protection against these complications. Even with very low levels of C-peptide, as low as 0.18 ng/mL, Type 1 Diabetes patients are considerably less prone to develop microvascular complications than those who are C-peptide-negative.

Exogenous regimens of injectable C-peptide have also demonstrated clinically relevant effects on peripheral nerves, kidney, and brain, confirming the protective benefit. Cell-based therapies have the advantage of co-secreting insulin and C-peptide, subsequently islet transplant reduces risk of hypoglycemic events, improves or slows progression of diabetic complications by providing a physiologic source of insulin, and increases quality of life measures.

Extending islet transplant to the majority of diabetic patients requires an implant strategy that: (i) supports alternative sources of islets or β-cells; (ii) prevents the instant blood-mediated inflammatory reaction and ongoing rejection resulting in β-cell dysfunction and destruction; (iii) eliminates major toxicity associated with chronic immunosuppression; (iv) is minimally invasive; (v) potentiates a biological environment that mimics typical physiologic milieu; and (vi) facilitates re-transplant or reload. Conventional microencapsulation technologies have addressed a number of these challenges, particularly (i)-(iv), but there is a significant gap between small animal models and effective translation to nonhuman primate (NHP) models and human clinical applications.

An apparatus and method is needed to overcome one or more of the above-discussed issues.

SUMMARY

In one embodiment of the disclosure, an interstitial fluid accumulation chamber is disclosed. The interstitial fluid accumulation chamber is configured to be implanted in a mammal for use as a protective environment for transplanted cells. The interstitial fluid accumulation chamber includes opposed first and second members, a cell isolation chamber, and a plurality of spaced-apart members. The opposed first and second members are disposed in spaced-apart relation. The cell isolation chamber is disposed within and in-between the opposed first and second members. The cell isolation chamber includes a filter which contains pores sized to allow interstitial fluid to enter the cell isolation chamber while preventing cells within the cell isolation chamber from leaving the cell isolation chamber. The plurality of spaced-apart members are disposed within and between the opposed first and second members. The plurality of spaced-apart members form a tortuous path which is configured to prevent tissue from growing within the interstitial fluid accumulation chamber.

In another embodiment of the disclosure, an interstitial fluid accumulation chamber is disclosed. The interstitial fluid accumulation chamber is configured to be implanted in a mammal for use as a protective environment for transplanted cells. The interstitial fluid accumulation chamber includes opposed plates, a cell isolation chamber, and a plurality of posts. The opposed plates are disposed in spaced-apart relation. The cell isolation chamber is disposed within and in-between the opposed first and second members. The cell isolation chamber includes a filter which contains pores sized to allow interstitial fluid to enter the cell isolation chamber while preventing cells within the cell isolation chamber from leaving the cell isolation chamber. The plurality of posts are disposed within and between the opposed plates. The plurality of posts form a tortuous path which is configured to prevent tissue from growing within the interstitial fluid accumulation chamber.

In still another embodiment of the disclosure, a method of using an interstitial fluid accumulation chamber is disclosed. In one step, the interstitial fluid accumulation chamber is disposed in a mammal. The interstitial fluid accumulation chamber comprises opposed first and second members, a cell isolation chamber, and a plurality of spaced-apart members. The opposed first and second members are disposed in spaced-apart relation. The cell isolation chamber is disposed within and in-between the opposed first and second members. The cell isolation chamber includes a filter. The plurality of spaced-apart members are disposed within and between the opposed first and second members. The plurality of spaced-apart members form a tortuous path. In another step, cells are disposed within the interstitial fluid accumulation chamber. In yet another step, interstitial fluid within the mammal flows through the tortuous path, through the filter, and into the cell isolation chamber. In another step, the tortuous path prevents tissue from growing within the interstitial fluid accumulation chamber. In still another step, the filter prevents the cells within the cell isolation chamber from leaving the cell isolation chamber.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
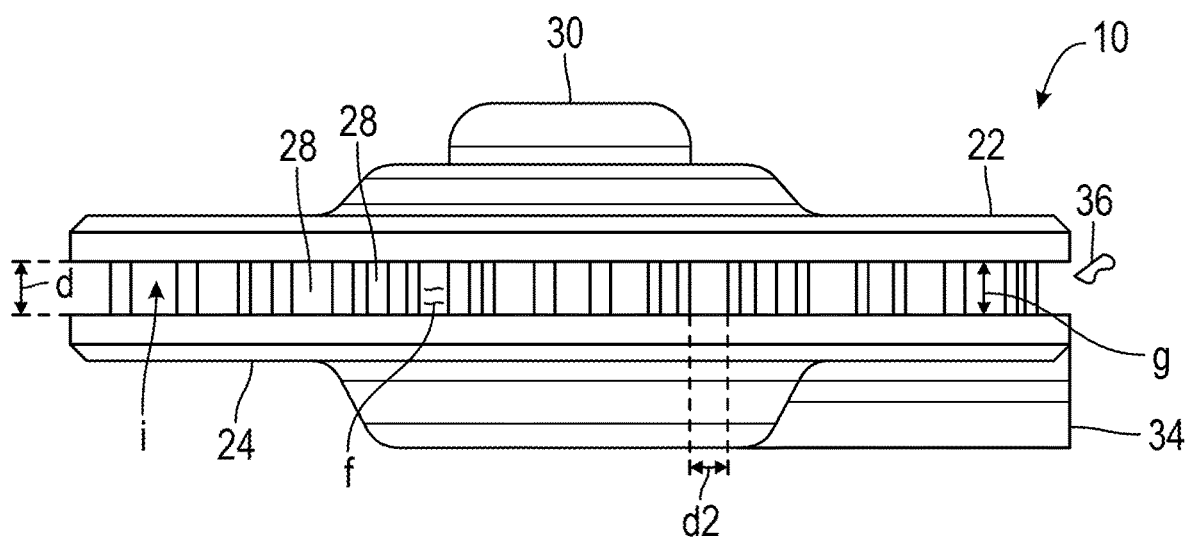
FIG. 1 illustrates a side view of one embodiment of an interstitial fluid accumulation chamber.

The instant disclosure uses the interstitial space as a direct implant site for β-cell transplant. The combination of an artificial interstitium fluid accumulation chamber with an omental pedicle is a strategy designed to establish highly efficient transcapillary exchange between the islet graft and direct insulin to the portal circulation in non-immunosuppressed nonhuman primates. Convective flow (perfusion) approaches are highly successful in supporting isolated islets in vitro and also in vivo using vascular shunting devices in combination with synthetic membranes. However, this has resulted in problems with safety (e.g. anticoagulation, thrombosis, bleed) and efficacy (e.g. membrane fouling) which have precluded further development.

A flow-based approach that does not disrupt central vasculature or subject patients to anticoagulation presents a major safety advantage. The artificial interstitium fluid accumulation chamber overcomes these limitations by continuously providing interstitial fluid (a physiologic transport medium) for bi-directional exchange of nutrients, waste, and signal factors to isolated islet cells and harnesses existing convective flow mechanisms between blood-interstitium-lymph compartments. Changes in interstitial fluid glucose levels are sensed by the graft, and insulin and glucagon secreted to the portal circulation thereby promoting downstream hepatic glucagon regulation. Sophisticated modifications of materials used in encapsulation have improved islet survival post-transplant, but protein release from the capsules attracts macrophages around capsules, triggering pericapsular overgrowth that diminishes oxygen and nutrient exchange across the membrane.

By properly facilitating passage of insulin, it is almost impossible to limit the passage of antigen, consequently a fundamentally new approach is needed to integrate immune control with near physiologic mass transfer. The interstitium plays a key role in peripheral tolerance by engaging the lymphatic system enabling direct communication between antigen and regulatory cytokines with the sentinel node. Flow alterations may also alter the artificial interstitium stroma, playing a key role in the immune microenvironment directly around the graft to create a local environment favoring regulation versus rejection, or a regenerative environment that provides appropriate signaling for cell maturation/differentiation to support neonatal islet or stem-cell derived products.

The complexity that a highly metabolically active islet introduces suggests that an integration of several concepts will ultimately be needed to unlock success. The artificial interstitium approach is designed to merge immunomodulation together with a favorable oxygen/nutrient profile, and polymers that mitigate islet anoikis. The design of the instant disclosure allows for unprecedented access to the islet graft via percutaneous needle to load, biopsy, retrieve, or evaluate conditions affecting graft performance. Serial graft biopsies are indispensable in improving understanding of intragraft events that determine engraftment, acceptance, and regeneration of transplanted islets and are critical for the development of refined islet delivery techniques.

Success of this approach has immediate implication for human islet allo-transplantation and facilitates 'unlimited' cell sources like xenogeneic porcine islets or stem cell-derived insulin-producing cells. The removal of interstitium stroma and reloading capability for replacement of exhausted grafts positively shifts the risk-benefit balance to expand therapy to many more patients with diabetes. There is even potential for this β-cell replacement therapy to treat a subset of patients with type 2 diabetes mellitus (T2DM), where β-cell insufficiency is a key part of the pathogenesis.

Figure 2:
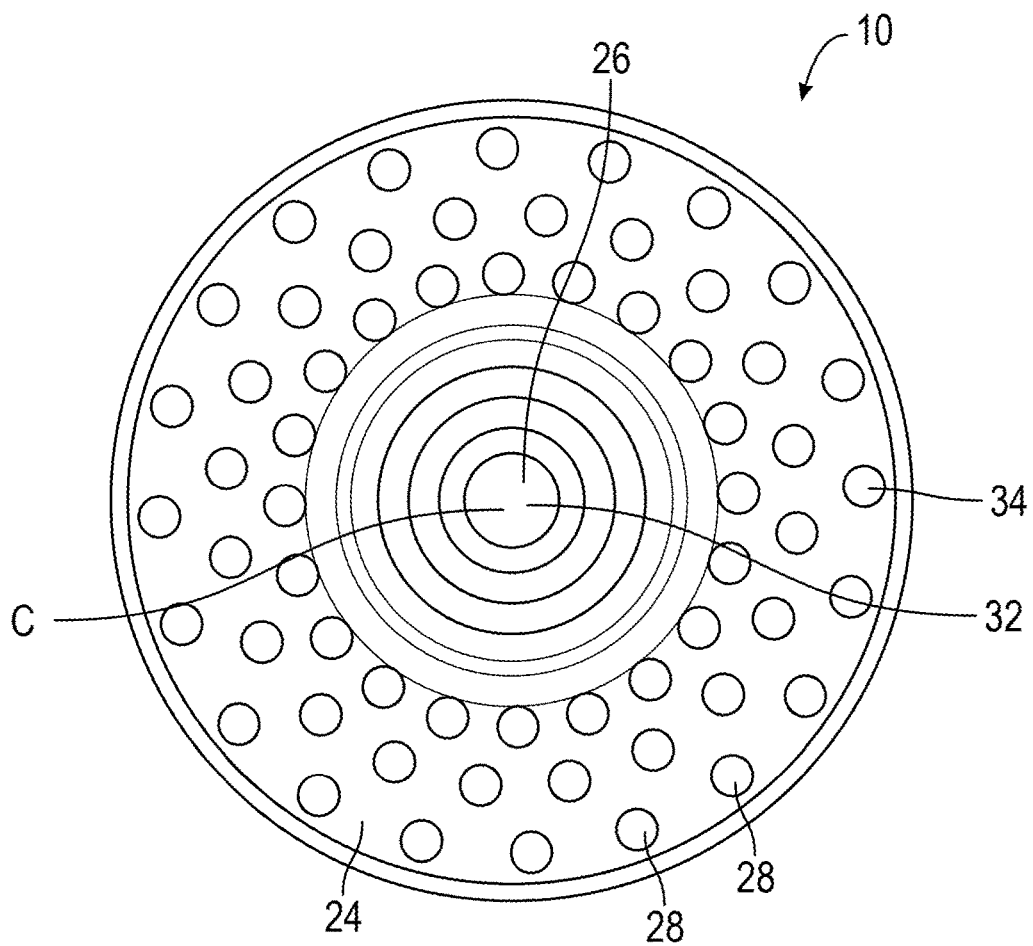
FIG. 2 illustrates a top view of the accumulation chamber of FIG. 1 with the top surface of the interstitial accumulation chamber being drawn as being transparent to show within the interstitial accumulation chamber.
Figure 3:
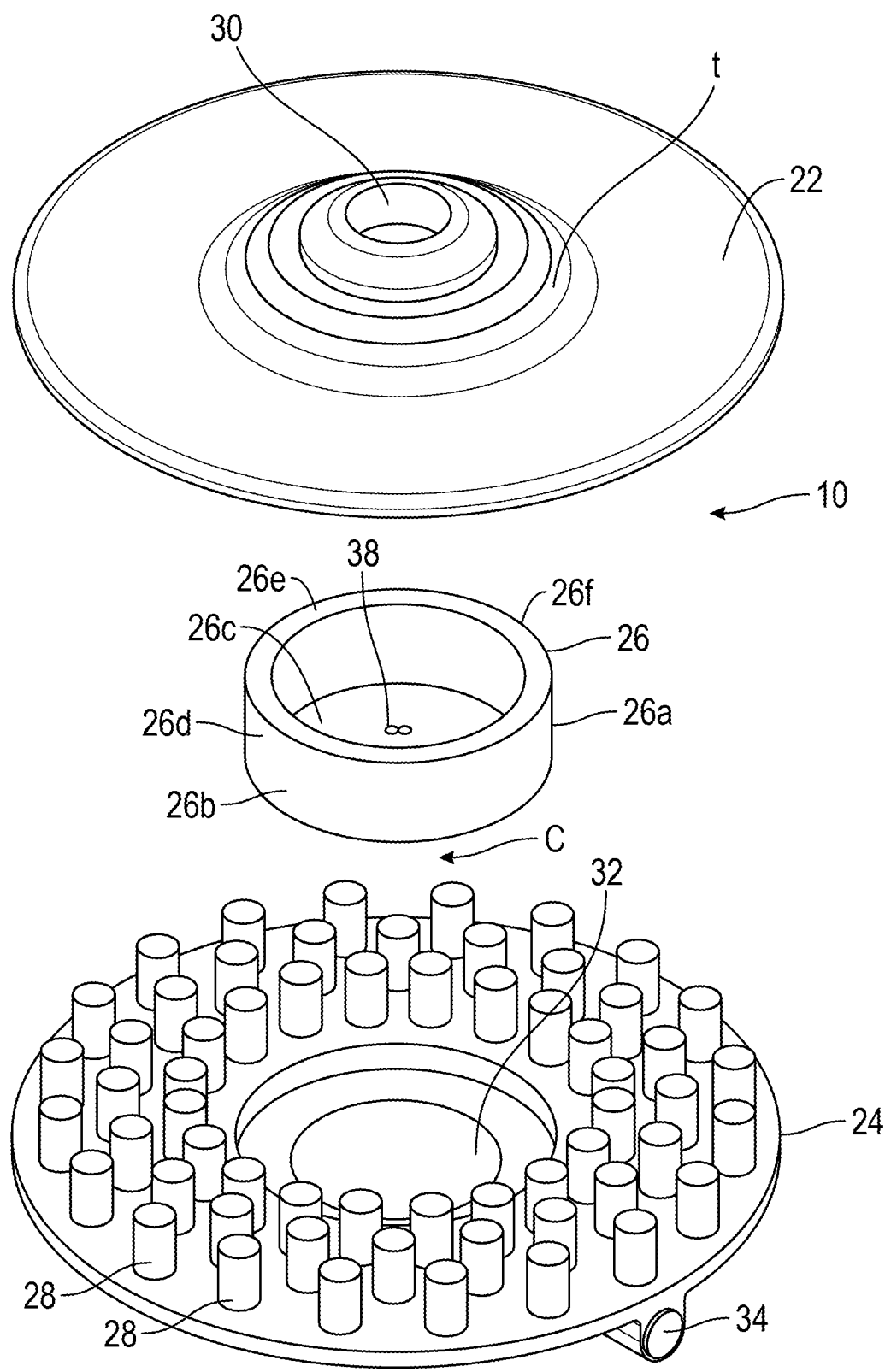
FIG. 3 illustrates a disassembled view of the accumulation chamber of FIG. 1.
Figure 4:
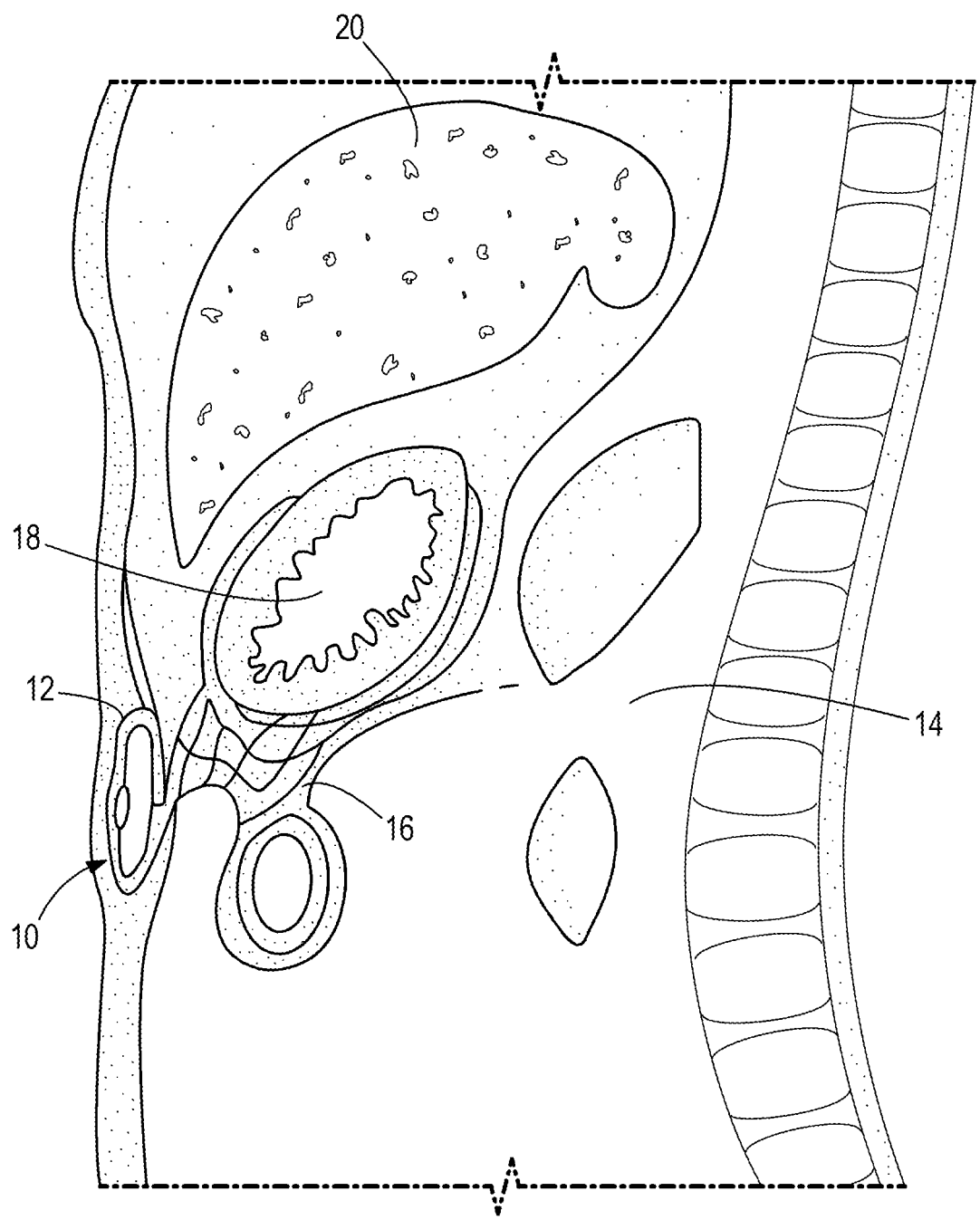
FIG. 4 illustrates the interstitial fluid accumulation chamber of FIG. 1 disposed in a subcutaneous pocket of a mammal disposed apart from the mammal's omentum, stomach, and liver.

FIG. 1 illustrates a side view of one embodiment of an interstitial fluid accumulation chamber 10. FIG. 2 illustrates a top view of the accumulation chamber of FIG. 1 with the top surface of the interstitial accumulation chamber being drawn as being transparent to show within the interstitial accumulation chamber. FIG. 3 illustrates a disassembled view of the accumulation chamber 10 of FIG. 1. FIG. 4 illustrates the interstitial fluid accumulation chamber 10 of FIG. 1 disposed in a subcutaneous pocket 12 of a mammal 14 disposed apart from the mammal's omentum 16, stomach 18, and liver 20.

As shown collectively in FIGS. 1-4, the interstitial fluid accumulation chamber 10 comprises opposed first and second members 22 and 24, a cell isolation chamber 26, a plurality of spaced-apart members 28, a septum 30, a drain 32, and a catheter 34. The interstitial fluid accumulation chamber 10 is configured to be implanted in a mammal 14 for use as a protective environment for transplanted cells 36. The opposed first and second members 22 and 24 comprise opposed plates in spaced-apart relation. In other embodiments, the opposed first and second members 22 and 24 may vary in size, shape, configuration, orientation, and type. The opposed first and second members 22 and 24 are spaced-apart at a distance d between the opposed first and second members 22 and 24 which prevents the tissue 36 from growing within the interstitial fluid accumulation chamber 10. The distance d is nominally 0.125 inches but can be anywhere in a range of 0.100 inches to 0.250 inches. In other embodiments, the distance d may vary. The size of the opposed first and second members 22 and 24 and the distance d between the opposed first and second members 22 and 24 is determined by the volume of the interstitial fluid f that needs to be accumulated within the interstitial fluid accumulation chamber 10. In one embodiment, the volume of interstitial fluid f that is accumulated is 2 ml. In other embodiments, the volume of interstitial fluid f accumulated may vary. The opposed first and second members 22 and 24 are molded components fabricated of pliable, medical grade silicone rubber (two-part liquid silicone rubber).

The cell isolation chamber 26 is disposed within and in-between the opposed first and second members 22 and 24. The cell isolation chamber 26 is disposed in a center c of the opposed first and second members 22 and 24. The cell isolation chamber 26 comprises a filter 26a which contains pores 26b sized to allow interstitial fluid f to enter the cell isolation chamber 26 while preventing cells 38 within the cell isolation chamber 26 from leaving the cell isolation chamber 26. The pores 26b are sized in a range of 20 to 150 microns. In other embodiments, the size of the pores 26b may vary. The filter 26a is cup-shaped. In other embodiments, the filter 26a may vary in size, shape, configuration, orientation, and type. The filter 26a comprises a bottom wall 26c, a side wall 26d which surrounds the bottom wall 26c, and an open top end 26e. The first member 22 is disposed against a top 26f of the side wall 26d covering the open top end 26e of the filter 26a. The cell isolation chamber 26 is cylindrical in shape, dictated by the fact that it is fabricated from a cup-shaped porous filter 26a, with an interior diameter of 0.625" (15.9 mm). The top surface t of the cell accumulation chamber 26 comprises the first member 22 fabricated of pliable, medical grade silicone with the septum 30, disposed in the first member 22, in alignment with the cell accumulation chamber 26. As described above, the bottom wall 26c and side wall 26d of the cell isolation chamber 26 is a sintered metal filter 26a designed to promote the free flow of interstitial fluid fin and out of the cell isolation chamber 26 while ensuring no cells 38 escape. The interstitial fluid f that flows into the cell isolation chamber 26 will diffuse out of the side wall 26d and the bottom wall 26c of the cell isolation chamber 26d through the filter 26a.

The plurality of spaced-apart members 28 are disposed within and between the opposed first and second members 22 and 24. The plurality of spaced-apart members 28 form a tortuous path which is configured to prevent tissue 36 from growing within the interstitial fluid accumulation chamber 10. The plurality of spaced-apart members 28 comprise a plurality of spaced-apart posts extending from and against the first member 22 to the second member 24 to hold the first and second opposed members 22 and 24 apart from one another. The plurality of spaced-apart members 28 are placed throughout the interior of the interstitial fluid accumulation chamber 10 to create a tortuous path for tissue 36 ingrowth and thus prevent the tissue 36 ingrowth from totally occluding the interior i of the interstitial fluid accumulation chamber 10 or the outlet comprising the drain 32 and catheter 34. Additionally, the distance d between the opposed first and second members 22 and 24 and the distance d2 between the plurality of spaced-apart members 28 prevents tissue 36 from growing over and throughout the opposed first and second members 22 and 24, thereby occluding them. The distance d2 is nominally 0.08 inches but can be in a range of 0.06 inches to 0.2 inches from edge to edge (i.e. closest distance between the plurality of spaced-apart members 28). In other embodiments, the distance d2 may vary. In other embodiments, the plurality of spaced-apart members 28 may vary in size, shape, configuration, orientation, and type.

As discussed, the first member 22 comprises a septum 30 disposed in alignment with the cell isolation chamber 26. The septum 30 comprises a penetrable port that provides access to the cell isolation chamber 26 for transplantation, retrieval, and evaluation of the cells 38. The drain 32 (~0.2 cc) of the cell isolation chamber 26 is connected to the catheter 34 at a location below the second member 24 and the cell isolation chamber 26. The opposed first and second members 22 and 24 are spaced apart such that the tissue 36 that would occlude a catheter or a small device will not grow across the gap g created between the first and second plates 22 and 24. While the opposed first and second members 22 and 24 may become engulfed with tissue 36, the center c of the interstitial fluid accumulation chamber 10 will remain open and allow for interstitial fluid f accumulation. As a result, the catheter 34 is protected from the tissue 36 invading.

The size and porosity of the material of the filter 26a may be adjusted as necessary to identify the best combination of pore 26b size and cell 38 survival and production. It is important to not only provide the living cells 38 with nutrients, but to also remove the waste products of the living cells 38. The catheter 34 is of sufficient diameter to prohibit as much fluid resistance as possible while being mindful of the size of the mammal 14 and surrounding adipose tissue. Poiseuille's Law teaches that fluid flow through a long, cylindrical tube is proportional to the fourth power of the radius ($r^4$). Thus, a doubling of the radius translates to a 16-fold increase in flow, or if the equation is rearranged, a 16-fold decrease in pressure.

The volume of the cell isolation chamber 26 is adjustable based on the diameter of the filter 26a, but initial units will be approximately 0.9 cc's. The flow-thru and dwell time for the interstitial fluid f will be determined by both the size of the pores 26b and the available surface area of the filter 26a.

As discussed, a small, compressed silicone septum (port-like feature) 30 is in alignment above the cell isolation chamber 26 to sample the contents of the cell isolation chamber 26 and to withdraw and replenish the cells 38 in the cell isolation chamber 26 as necessary. Angiogenesis drugs can be injected/infused through the septum/port 30 to promote vascularization outside of the cell isolation chamber 26. Vascularization is important for communications between the cells 38 and the blood stream of the mammal 14. Ideally, this communication will be both ways, from the cells 38 out and from the vasculature in, to elicit the production of the enzymes designated by the transplanted cells 38. Additionally, a custom vascular access port may be attached to the catheter 34 for further sampling and priming of the interstitial fluid accumulation chamber 10. Priming may be necessary to induce initial flow.

In other embodiments, the interstitial fluid accumulation chamber 10 may vary in size, shape, configuration, orientation, and type.

Figure 5:
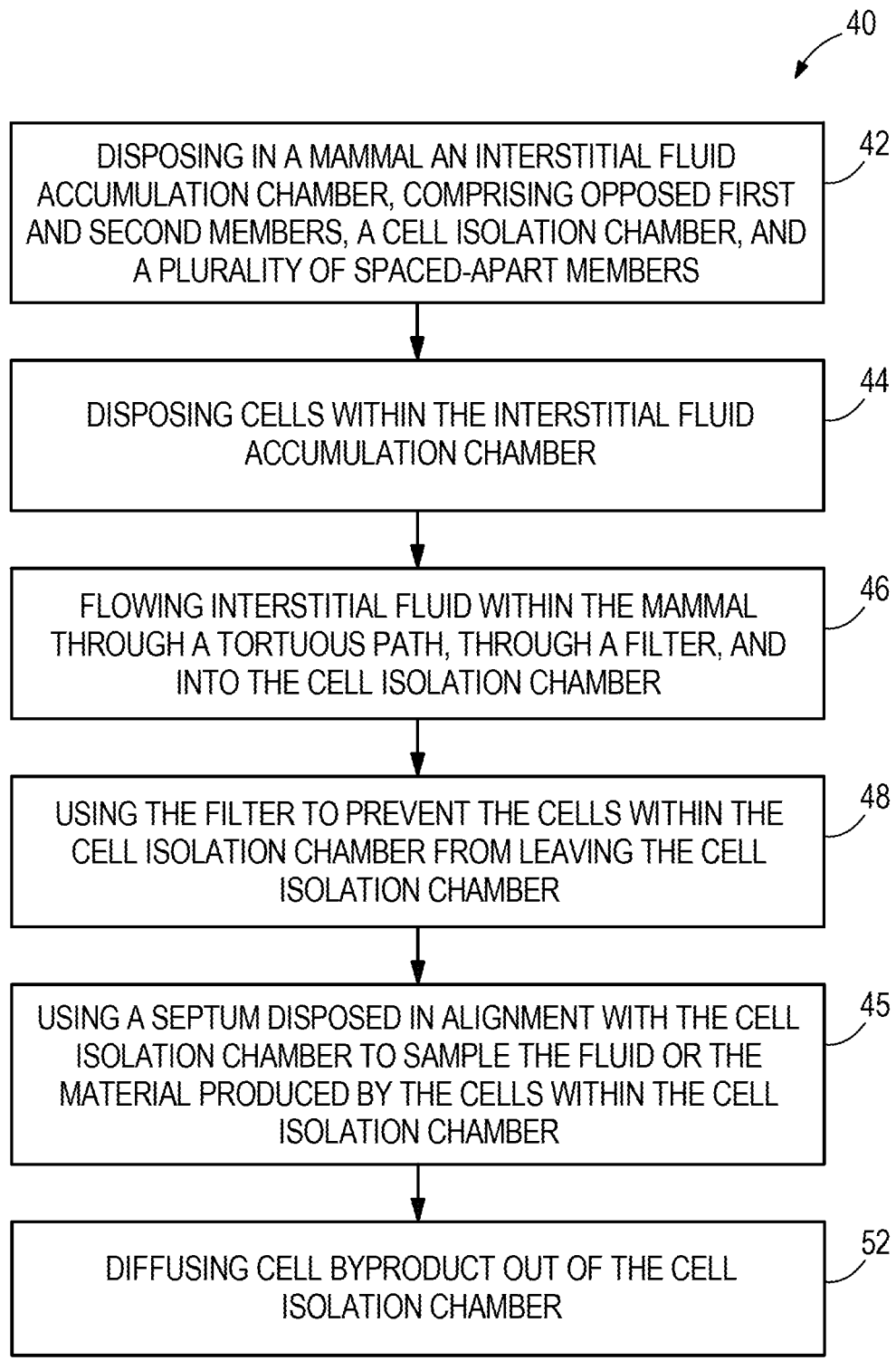
FIG. 5 is a flowchart illustrating one embodiment of a method of using an interstitial fluid accumulation chamber.

FIG. 5 is a flowchart illustrating one embodiment of a method 40 of using an interstitial fluid accumulation chamber. The method 40 may utilize any of the embodiments of the interstitial fluid accumulation chamber 10 of the disclosure. In other embodiments, the method 40 may utilize varying types of interstitial fluid accumulation chambers.

In step 42, the interstitial fluid accumulation chamber is disposed in a mammal. The interstitial fluid accumulation chamber comprises opposed first and second members, a cell isolation chamber, and a plurality of spaced-apart members. The opposed first and second members are in spaced-apart relation. The cell isolation chamber is disposed within and in-between the opposed first and second members. The cell isolation chamber comprises a filter. The plurality of spaced-apart members are disposed within and between the opposed first and second members. The plurality of spaced-apart members form a tortuous path. In step 44, cells are disposed within the interstitial fluid accumulation chamber. In step 46, interstitial fluid within the mammal flows through the tortuous path, through the filter, and into the cell isolation chamber. In one embodiment, in step 46 a distance between the opposed first and second members prevents the tissue from growing within the interstitial fluid accumulation chamber, and the tortuous path prevents tissue from growing within the interstitial fluid accumulation chamber. In step 48, the filter prevents the cells within the cell isolation chamber from leaving the cell isolation chamber. In step 50, the cells produce fluid or material within the cell isolation chambers, and the fluid or the material produced by the cells within the cell isolation chamber is sampled through a septum disposed in alignment with the cell isolation chamber. In step 52, fluid or material produced by the cells within the cell isolation chamber is distributed from the cell isolation chamber, through a drain, through a catheter, to a location within the mammal. Additionally, in step 52 cell byproduct also diffuses out of the cell isolation chamber due to fluid kinetics. In step 54, the cells within the cell isolation chamber are withdrawn or replenished through the septum disposed in alignment with the cell isolation chamber.

In other embodiments, one or more steps of the method 40 may vary in substance or order, one or more steps of the method 40 may not be followed, or one or more additional steps may be added.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. An interstitial fluid accumulation chamber configured to be implanted in a mammal for use as a protective environment for transplanted cells comprising:
   opposed first and second members in spaced-apart relation;
   a cell isolation chamber disposed within and in-between the opposed first and second members, the cell isolation chamber comprising a filter extending from the first member to the second member, the filter containing pores sized to allow interstitial fluid to enter the cell isolation chamber while preventing cells within the cell isolation chamber from leaving the cell isolation chamber; and
   a plurality of spaced-apart members disposed within and between the opposed first and second members, the plurality of spaced-apart members forming a tortuous path which is configured to prevent tissue from growing within the interstitial fluid accumulation chamber;
   wherein the plurality of spaced-apart members are disposed around the filter.

2. The interstitial fluid accumulation chamber of claim 1 wherein the opposed first and second members are spaced-apart at a distance between the first and second members which prevents the tissue from growing within the interstitial fluid accumulation chamber.

3. The interstitial fluid accumulation chamber of claim 1 wherein the opposed first and second members comprise opposed plates.

4. The interstitial fluid accumulation chamber of claim 1 wherein the filter comprises a bottom wall, a side wall which surrounds the bottom wall, and an open top end.

5. The interstitial fluid accumulation chamber of claim 4 wherein the first member is disposed against a top of the side wall, the first member covering the open top end of the filter.

6. The interstitial fluid accumulation chamber of claim 1 wherein the filter is cup-shaped.

7. The interstitial fluid accumulation chamber of claim 1 wherein the pores of the filter are sized in a range of 20 to 150 microns.

8. The interstitial fluid accumulation chamber of claim 1 wherein the cell isolation chamber is disposed in a center of the opposed first and second members.

9. The interstitial fluid accumulation chamber of claim 1 wherein the first member comprises a septum disposed in alignment with the cell isolation chamber.

10. The interstitial fluid accumulation chamber of claim 1 wherein the cell isolation chamber is connected to a catheter.

11. The interstitial fluid accumulation chamber of claim 1 wherein the plurality of spaced-apart members comprise a plurality of spaced-apart posts extending from the first member to the second member.

12. An interstitial fluid accumulation chamber configured to be implanted in a mammal for use as a protective environment for transplanted cells comprising:
    opposed plates in spaced-apart relation;
    a cell isolation chamber disposed within and in-between the opposed plates, the cell isolation chamber comprising a filter extending from one of the opposed plates to the other of the opposed plates, the filter containing pores sized to allow interstitial fluid to enter the cell isolation chamber while preventing cells within the cell isolation chamber from leaving the cell isolation chamber; and
    a plurality of posts disposed within, between, and against the opposed plates, the plurality of posts forming a tortuous path which is configured to prevent tissue from growing within the interstitial fluid accumulation chamber;
    wherein the plurality of posts are disposed around the filter.

13. The interstitial fluid accumulation chamber of claim 12 wherein the opposed plates are spaced-apart at a distance between the opposed plates which prevents the tissue from growing within the interstitial fluid accumulation chamber.

14. The interstitial fluid accumulation chamber of claim 12 wherein the filter comprises a bottom wall, a side wall which surrounds the bottom wall, and an open top end, the one of the opposed plates disposed against a top of the side wall and covering the open top end of the filter.

15. The interstitial fluid accumulation chamber of claim 12 wherein the one of the opposed plates comprises a septum disposed in alignment with the cell isolation chamber.

16. A method of using an interstitial fluid accumulation chamber comprising:

disposing the interstitial fluid accumulation chamber in a mammal, the interstitial fluid accumulation chamber comprising: opposed first and second members in spaced-apart relation; a cell isolation chamber disposed within and in-between the opposed first and second members, the cell isolation chamber comprising a filter extending from the first member to the second member; and a plurality of spaced-apart members disposed within and between the opposed first and second members, the plurality of spaced-apart members forming a tortuous path; wherein the opposed first and second members are disposed around the filter;

disposing cells within the interstitial fluid accumulation chamber;

interstitial fluid within the mammal flowing through the tortuous path, through the filter, and into the cell isolation chamber;

the tortuous path preventing tissue from growing within the interstitial fluid accumulation chamber; and the filter preventing the cells within the cell isolation chamber from leaving the cell isolation chamber.

17. The method of claim 16 further comprising a distance between the opposed first and second members preventing the tissue from growing within the interstitial fluid accumulation chamber.

18. The method of claim 16 further comprising withdrawing or replenishing the cells within the cell isolation chamber through a septum disposed in alignment with the cell isolation chamber.

19. The method of claim 16 further comprising the cells producing fluid or material within the cell isolation chamber, and sampling the fluid or material disposed within the cell isolation chamber through a septum disposed in alignment with the cell isolation chamber.

20. The method of claim 16 further comprising the cells within the cell isolation chamber producing fluid or material, and distributing the fluid or material from the cell isolation chamber, through a catheter, to a location within the mammal.

21. The interstitial fluid accumulation chamber of claim 10 wherein the catheter is disposed within the second member below a bottom wall of the filter.

22. The interstitial fluid accumulation chamber of claim 12 wherein the cell isolation chamber is connected to a catheter, the catheter disposed within the other of the opposed plates below a bottom wall of the filter.

23. The method of claim 20 wherein the catheter is disposed within the second member below a bottom wall of the filter.

* * * * *